United States Patent [19]

Glenn

[11] 4,313,444
[45] Feb. 2, 1982

[54] METHOD AND APPARATUS FOR ULTRASONIC DOPPLER DETECTION

[75] Inventor: William E. Glenn, Fort Lauderdale, Fla.

[73] Assignee: New York Institute of Technology, Old Westbury, N.Y.

[21] Appl. No.: 38,661

[22] Filed: May 14, 1979

[51] Int. Cl.³ .............................................. A61B 5/02
[52] U.S. Cl. ................................................... 128/663
[58] Field of Search .............................. 128/660–663; 73/194 A

[56] References Cited

U.S. PATENT DOCUMENTS

| | | | |
|---|---|---|---|
| 3,550,070 | 12/1970 | McLeod | 128/663 |
| 3,554,030 | 1/1971 | Perouneau | 128/663 |
| 3,640,271 | 2/1972 | Horton | 128/662 |
| 3,675,192 | 7/1972 | Fohrbach | 128/663 |
| 3,766,517 | 10/1973 | Fohrbach | 73/194 A |
| 3,987,673 | 10/1976 | Hansen | 128/663 |
| 4,062,237 | 12/1977 | Fox | 73/194 A |
| 4,097,835 | 6/1978 | Green | 128/663 |
| 4,137,777 | 2/1979 | Hoverl et al. | 128/660 |
| 4,141,347 | 2/1979 | Green et al. | 738/627 |
| 4,182,173 | 1/1980 | Papadofrangakis et al. | 128/663 |

FOREIGN PATENT DOCUMENTS 1398022 6/1975 United Kingdom ................ 128/663

OTHER PUBLICATIONS

Fox, M. D. et al., "Crossed Beam Concept for UTS Doppler Flow Detection", Proc. 3rd Ann. New Eng. Bioengr. Conf., May 9–10, 1975, pp. 1–8.
Reid, J. M. et al, "UTS Doppler Technique for Imaging Blood Vessels", Science (USA), vol. 176, No. 4040, pp. 1235–1236, Jun. 16, 1972.
Boker, D. W., "Pulsed UTS Doppler Blood-Flow Sensing", IEEE Trans. on Sonics & Ultrasonics, vol. SU-17, No. 3 (Jul. 1970).
McCarty, K. et al., "The UTS Doppler Shift Flowmeter-A New Development", Biomed. Engr. (Aug. 1974).

Primary Examiner—Robert W. Michell
Assistant Examiner—Francis J. Jaworski
Attorney, Agent, or Firm—Martin Novack

[57] ABSTRACT

The disclosure is directed to a method and apparatus for determining the velocity of a material within a body, and which is also capable of simultaneously imaging sections of the body. In the velocity-determined method, a focused beam of ultrasound is directed, over a given aperture, toward the skin of the body, the central ray of the focused ultrasound beam being oriented substantially normal to the skin. The ultrasound beam reflected from the body is received over the same aperture. Preferably, the steps of directing and receiving the ultrasound employ the same single transducer, and focusing is achieved using a focusing lens. Beat frequency signals are detected in the received beam, these signals resulting from the beating of Doppler effect components reflected from the moving material, for example, blood corpuscles of moving blood within the body. Velocity-representative indications, for example, audio or video presentations, are then generated as a function of the detected beat frequency signals. The detected beat frequency signals are beats between Doppler effected portions of the received ultrasound beam which have frequency components above and below the frequency of the originally directed ultrasound beam.

31 Claims, 6 Drawing Figures

METHOD AND APPARATUS FOR ULTRASONIC DOPPLER DETECTION

BACKGROUND OF THE INVENTION

This invention relates to ultrasonic systems and, more particularly, to apparatus for imaging sections of a body by transmitting ultrasonic energy into the body and determining the characteristics of the ultrasonic energy reflected therefrom, the apparatus having the capability of detecting the velocity of motion of material within the body.

In recent years ultrasonic techniques have become more prevalent in clinical diagnosis. Such techniques have been utilized for some time in the field of obstetrics, neurology and cardiology, and are becoming increasingly important in the visualization of a number of different body portions, for example, the scanning of breasts to detect tumors.

Various fundamental factors have given rise to the increased use of ultrasonic techniques. Ultrasound differs from other forms of radiation in its interaction with living systems in that it has the nature of a mechanical wave. Accordingly, information is available from its use which is of a different nature than that obtained by other methods and it is found to be complementary to other diagnostic methods, such as those employing X-rays. Also, the risk of tissue damage using ultrasound appears to be much less than the apparent risk associated with ionizing radiations such as X-rays.

The majority of diagnostic techniques using ultrasound are based on the pulse-echo method wherein pulses of ultrasonic energy are periodically generated by a suitable piezoelectric transducer such as a lead zirconate-titanate ceramic. Each short pulse of ultrasonic energy is focused to a narrow beam which is transmitted into the patient's body wherein it eventually encounters interfaces between various different structures of the body. When there is a characteristic impedance mismatch at an interface, a portion of the ultrasonic energy is reflected at the boundary back toward the transducer. After generation of the pulse, the transducer operates in a "listening" mode wherein it converts received reflected energy or "echoes" from the body back into electrical signals. The time of arrival of these echoes depends on the ranges of the interfaces encountered and the propagation velocity of the ultrasound. Also, the amplitude of the echo is indicative of the reflection properties of the interface and, accordingly, of the nature of the characteristic structures forming the interface.

There are various ways in which the information in the received echoes can be usefully presented. In one common technique, the electrical signal representative of detected echoes are amplified and applied to the vertical deflection plates of a cathode ray display. The output of a time-base generator is applied to the horizontal deflection plates. Continuous repetition of the pulse/echo process in sychronism with the time-base signals produces a continuous display, called an "A-scan", in which time is proportional to range, and deflections in the vertical direction represent the presence of interfaces. The height of these vertical deflections is representative of echo strength.

Another common form of display is the so-called "B-scan" wherein the echo information is of a form more similar to conventional television display; i.e., the received echo signals are utilized to modulate the brightness of the display at each point scanned. This type of display is found especially useful when the ultrasonic energy is scanned transverse the body so that individual "ranging" information yields individual scan lines on the display, and successive transverse positions are utilized to obtain successive scan lines on the display. The two-dimensional B-scan technique yields a cross-sectional picture in the plane of the scan, and the resultant display can be viewed directly or recorded photographically or on magnetic tape.

In addition to its application for imaging internal features of a body, as described, ultrasound has also been employed for measuring the velocity of motion of material within a body by employing established Doppler detection techniques. Typically, an ultrasound beam is directed such that a component thereof is in the direction (or opposed to the direction) of flow of blood moving in a body. As is well known, the returning ultrasound echoes will have a Doppler shifted frequency component that is a function of the blood velocity.

It has been recognized that it would be highly desirable to have a single equipment which has a capability of both ultrasonic imaging and ultrasonic blood velocity measurement. With such an integrated equipment the user could, for example, locate a specific position in a blood vessel using a displayed image, and also obtain a measure of blood velocity (or, once geometry is known, flow rate) at the specific position. In one recently developed scheme, an ultrasonic Doppler flow meter subsystem is used in conjunction with a two dimensional B-scan ultrasonic imaging system. The imaging system utilizes an array of one or more transducers that is directed approximately normal to the patient's skin, as is conventional. To obtain Doppler flow measurements, at least one separate transducer is mounted on the same assembly as the B-scan system. This separate transducer is oriented at an angle with respect to the perpendicular to the skin, so that the beam emitted therefrom has a component in the direction of flow of blood vessels flowing beneath the skin. By processing the output of the separate transducer, a range-gated Doppler signal can be obtained and presented (e.g. an audio or video presentation) which represents the flow velocity of blood at the range-gated position at which the separate transducer is aimed. It would be desirable to have the B-scan image presented simultaneously with the Doppler information from the same region in the body. However, interference can occur between the two separate ultrasound subsystems if they are operated together. Accordingly, in order to obtain simultaneous presentation of information without excessive interference, one prior art scheme stores and repetitively presents the B-scan image while the separate transducer is operative to obtain Doppler flow information for "simultaneous" presentation. However, in addition to the complexity and cost of such a scheme, problems can arise from movements of the scanner head during the time that the Doppler subsystem is active, since such movements result in "misalignment" of the Doppler information with the stored B-scan information that is being presented.

It is among the objects of this invention to provide an improved Doppler detection system and an advantageous combination of an ultrasonic imaging subsystem and a Doppler flow meter subsystem that overcomes the type of problems set forth and provides a more efficient and less expensive technique for simultaneous presentation of useful information.

SUMMARY OF THE INVENTION

The present invention is directed to a method and apparatus for determining the velocity of a material within a body, and which is also capable of simultaneously imaging sections of the body. In the velocity-determining method, a focused beam of ultrasound is directed, over a given aperture, toward the skin of the body, the central ray of the focused ultrasound beam being oriented substantially normal to the skin. The ultrasound beam reflected from the body is received over the same aperture. Preferably, the steps of directing and receiving the ultrasound employ the same single transducer, and focusing is achieved using a focusing lens. Beat frequency signals are detected in the received beam, these signals resulting from the beating of Doppler effect components reflected from the moving material, for example, blood corpuscles of moving blood within the body. Velocity-representative indications, for example, audio or video presentations, are then generated as a function of the detected beat frequency signals. The detected beat frequency signals are beats between Doppler effected portions of the received ultrasound beam which have frequency components above and below the frequency of the originally directed ultrasound beam.

In accordance with a feature of the invention, the technique for obtaining Doppler blood flow information is combined with a technique for simultaneously imaging sections of the body using the same transducer. An apparatus hereof for simultaneously imaging sections of a body and detecting the velocity of blood within the body includes timing means for generating timing signals, and energizing/receiving means alternately operative in response to timing signals. A transducer coupled to the energizing/receiving means converts electrical energy into a beam of ultrasound energy and vice versa. A focusing means focuses the beam of ultrasound energy, and it is directed in a direction substantially normal to the skin of the body. Reflected ultrasound echoes are directed back toward the transducer. A first processing means is responsive to the output of the energizing/receiving means for generating image-representative signals representative of the ultrasound echo characteristics of the body. A second processing means is also responsive to the output of the energizing/receiving means for detecting beat frequency signals resulting from the beating of Doppler effect components reflected from moving blood within the body. Velocity-representative indications are then generated as a function of the detected beat frequency signals. As will be described, the transducer, focusing means, and directing means are preferably contained in a fluid-filled portable module. The directing means may include a scanning mirror in the fluid, or may merely comprise the appropriate geometrical mounting of the transducer within its housing or portable module such that the central ray of the focused ultrasound beam is directed substantially normal to the skin (as is typical for the case for B-scan imaging, but is atypical for Doppler blood flow detection).

Further features and advantages of the invention will become more readily apparent from the following detailed description when taken in conjunction with the accompanying drawings.

DESCRIPTION OF THE PREFERRED EMBODIMENT

Figure 1:
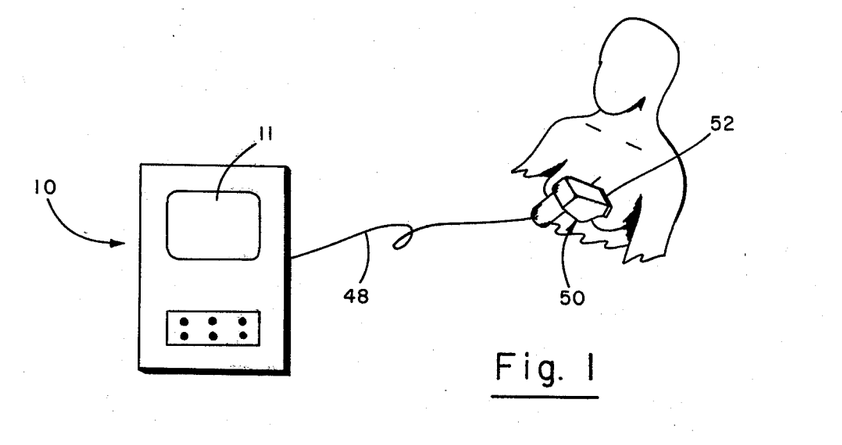
FIG. 1 illustrates the operation of an apparatus which employs the improvements of the invention.

Referring to FIG. 1, there is shown an illustration of a scanning apparatus which employs improvements of the invention. A console 10 is provided with a display 11 which may typically be a cathode ray tube television-type display, and a suitable control panel. A video tape recorder or suitable photographic means may also be included in the console. The console will also typically house power supplies and portions of the timing and processing circuitry of the system, to be described. A portable scanning module or probe 50 (shown in FIG. 2) is coupled to the console by cable 48. The scanning module has a window 52 at one end thereof through which an investigating ultrasound beam is emitted and a reflected beam is received. During operation of the apparatus, the scanning module 50 is hand held to position the window 52 over a part of the body to be imaged. For example, in FIG. 1, the scanning module is positioned such that a cross-section through a breast will be obtained. Imaging of other sections through the breast or other portions of the body is readily attained by moving the probe to the desired position and orientation, relative orientation of the scanning window determining the angle of the cross-section taken.

Figure 3:
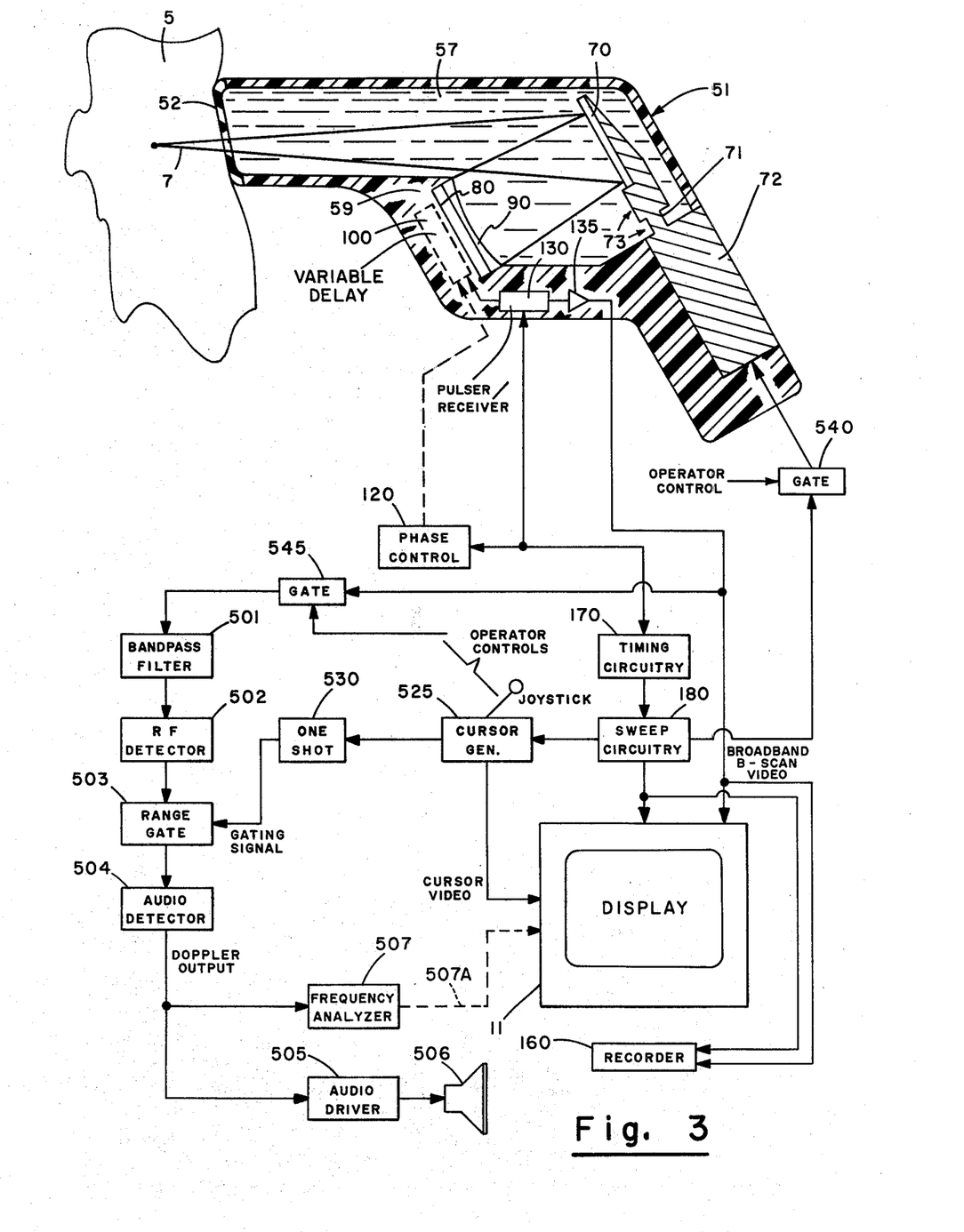
FIG. 3 shows a cross-sectional view of the scanning module of FIG. 2 as taken through a section defined by arrows 3-3, along with diagrams of portions of circuitry therein and in the accompanying console.

Referring to FIG. 3, there is shown a cross-sectional view of a portion of the scanning module or probe 50 along with diagrams of portions of the circuitry therein and in console 10 used in conjunction therewith. A fluid-tight enclosure 51, which may be formed of a sturdy plastic, has scanning window 52 at the front end thereof. The enclosure 51 is filled with a suitable fluid 57, for example, water. In the present embodiment the scanning window 52 is relatively flat and may be formed of any suitable material, for example, methyl methacrylate or nylon. A reflective scanner 70, which is flat in the present embodiment but which may be curved to provide focusing if desired, is positioned at the approximate rear of the enclosure 51 and substantially faces the window 52. The scanner 70 is mounted on a shaft 71 which passes through a suitable seal and is connected to an electric motor 72 which is mounted in a recess in enclosure 51 and is driven to provide the desired oscillatory motion of scanner 70, as depicted by curved two-headed arrow 73.

An ultrasonic transducer 80 is mounted in a compartment 59 of enclosure 51, the transducer being mounted relatively frontwardly of reflective scanner 70 in the module 50 with the ultrasound-emitting face of the transducer generally facing rearwardly in the module 50 and being directed toward the reflective scanner 70. The transducer 80 is positioned such that the ultrasound beam which it emits is reflected by the scanner 70 to double back past transducer 80 before passing through the window 52. The scanner 70 preferably has a reflective surface formed of a material such as sapphire which, in conjunction with the adjacent water, exhibits a relatively small critical angle. The result is that even a beam impinging almost directly on the reflector surface will be reflected and not pass through the reflector.

A pulser/receiver circuit 130 alternatively provides energizing pulses to and receives echo signals from the transducer 80. As used herein, the term pulser/receiver is intended to include any combined or separate circuits for producing the energizing signals for the transducer and receiving echo signals therefrom. If dynamic focusing is employed, the transducer 80 may be segmented and the pulser/receiver circuitry 130 may be coupled to the segments of transducer 80 via variable delay circuitry 100, shown in dashed line. The pulser/receiver circuitry 130 and the variable delay circuitry 100 (if present) are typically, although not necessarily, located in the scanning module 50, for example within the compartment 59. The receiver portion of circuit 130 is coupled, via a preamp 135, which is preferably located in portable scanning module 50, to display 11 and to recorder 160, which may be any suitable recording, memory, and/or photographic means, for example, a video tape recorder. Timing circuitry 170 generates timing signals which synchronize operation of the system, the timing signals being coupled to pulser/receiver 130 and also to sweep circuitry 180 which generates the signals that control the oscillations of scanner 70 and the vertical and horizontal sync signals for the display 11 and recorder 160. If dynamic focusing is employed, as described in copending U.S. patent application Ser. No. 000,430, assigned to the same assignee as the present application, the timing signals may also be coupled to phase control circuitry 120 which produces signals that control the variation of the delays in variable delay circuit 100.

A lens 90, which typically has a relatively flat surface bonded to the transducer and a curved concave surface which provides axially symmetric focusing, is employed in the scanning module 50. The lens may be formed of a plastic material with the material being selected in accordance with the principles set forth in U.S. Pat. No. 3,958,559, assigned to the same assignee as the present application. As disclosed in that patent, by selecting the lens material in accordance with specified parameters, "apodization" is achieved; i.e., undesired side lobes, caused by factors such as finite transducer size, are minimized. Further, as disclosed in the referenced patent, the lens may have a generally elliptical contour to attain advantageous characteristics. If desired, however, alternative means of focusing can be employed, such as electronic focusing using a segmented transducer, or providing curvature in the transducer or reflector surface.

Operation of the portion of the system described so far is as follows: Upon command from the timing circuits the pulser in circuitry 130 generates pulses which excite the transducer 80, the segments of transducer 80 being excited via variable delay circuitry 100, under control of phase control circuitry, when dynamic focusing is employed. (As is known in the art, the depth of focus can be varied electronically in a dynamically focused system by imparting predetermined delays or phase changes to different segments of the transducer 80. In such case the ultrasound pulse is typically launched with the variable delay circuitry set so that the transmitted beam is focused at a point which is between the center of the field and the deepest point within the body at which an image is being sought.) The beam of ultrasound resulting from pulsing the transducer is reflected by reflector 70 through the window 52 and into the body 5. The timing circuitry now causes the pulser/receiver 130 to switch into a "receive" or "listen" mode. (If dynamic focusing is employed, a cycle of the phase control circuitry 120 is activated.) Now, as the ultrasound echoes are received from the body via window 52 and reflected off scanner 70 toward transducer 80, the transducer serves to convert the received ultrasound energy into electrical signals. (Again, for a dynamic focusing implementation, the transducer segments serve to convert the received ultrasonic energy into electrical signals which are combined in proper phase relationship for focusing on particular reflection origination points in the range of depths being investigated.) For a two-dimensional "B-scan" display, a sweep over the range of depth corresponds to a horizontal scanline of the display, so the timing signals from circuitry 170 synchronize the horizontal sync of the display such that the active portion of one scanline of the display corresponds to the time of arrival of echoes from a given range within the body 5, typically from the patient's skin up to a fixed preselected depth in the body. The second dimension of the desired cross-sectional image is attained by the slower mechanical scan of reflective scanner 70 which is synchronized with the vertical sweep rate of the display and recorder by the sweep circuitry 180. The received signals are coupled through amplifier 140 to display 11 wherein the received signals modulate the brightness of the scanning raster to obtain the desired cross-sectional image, with each scanline of the display representing a depth echo profile of the body for a particular angular orientation of the scanner 70. The received signals are also recorded on the video tape recorder 160.

The subsystem for detecting the velocity of moving material, typically blood, within the body, will next be described. The output of preamplifier 135 is also coupled to an operator-controllable gate 545 whose output is coupled to a bandpass filter 501. The filter has about a 1 MHz bandpass centered at about 8 MHz, the operating frequency of transducer 80 in the present embodiment. The output of bandpass filter 501 is coupled to an RF detector 502, whose output is, in turn, coupled to a gate 503 which serves as a range gate. The gate 503 has an enable terminal controlled by the output of a cursor generator 525 via a one-shot multivibrator 530. The output of range gate 503 is coupled to an audio detector 504 whose output is, in turn, coupled to an audio driver 505 and to a frequency analyzer 507. Audio driver 505 is coupled to speaker 506. Frequency analyzer 507 may have its own display (not shown) or may be used to generate a video signal 507A which is coupled to display 11 to produce a video indication of the detected Doppler signal. Cursor generators are very well known in the art and will not be detailed herein. Briefly, however, the cursor generator 525 receives synchronizing signals from sweep circuits 180, and has a manual control, such as dial or "joy stick", which selects a reference point in the video display field. A video signal for presenting this point; i.e., the cursor "dot", is coupled to video display 11. As stated, the cursor video is also coupled to the enable terminal of gate 503 via one-shot multivibrator 530. A gate 540, which may be under common operator control with gate 545, is adapted to inactivate the sweep signals which control the motor 72.

Briefly, operation of the Doppler subsystem hereof is as follows: The operator selects a position of the cursor dot on display 11 using the joystick input of cursor generator 525. The operator also controls gate 545 to enable passage of the preamplifier 135 output to the processing circuitry beginning with filter 501. In the present embodiment the operator also controls gate 540 to disable the scan of mirror 70 so that the mirror stops at a predetermined "rest" position, typically at the center of its scanning sector. Doppler effect information is detected and processed by circuitry 501-504 and presented via speaker 506 and/or frequency analyzer 507, as will be described further hereinbelow. At the same time, B-scan information in one dimension (i.e., depth only, since the scanner 70 has been stopped) continues to be presented on display 11 via the conventional B-scan subsystem.

Figure 4:
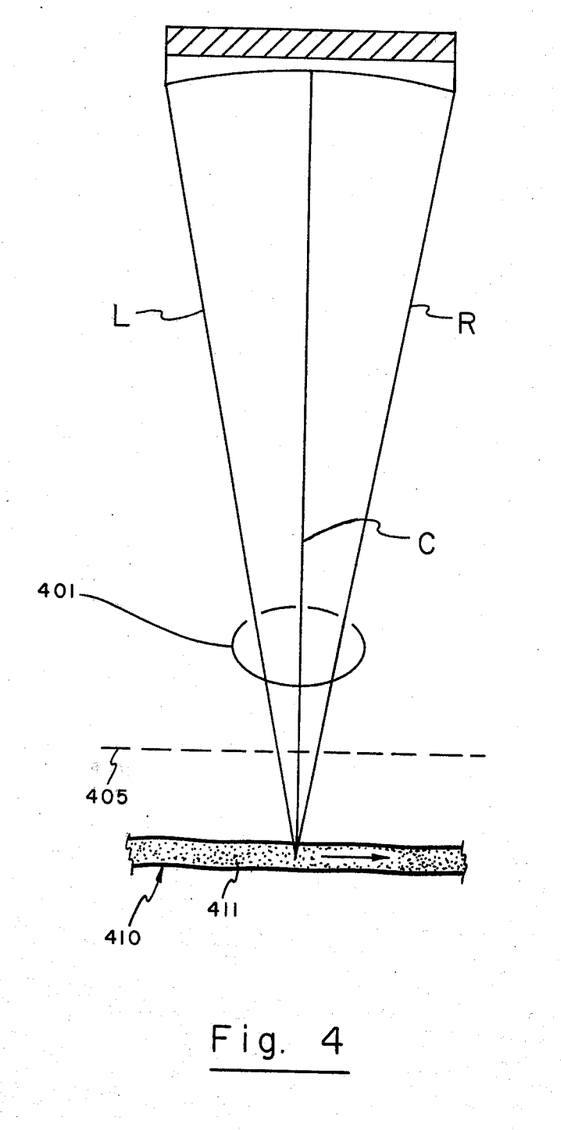
FIG. 4 is a simplified diagram of a focused ultrasound beam impinging on a subcutaneous blood vessel.

Before describing further details of operation of the Doppler detection subsystem, and to gain an understanding, in simplified terms, of the Doppler effect detected using the techniques hereof, reference is made to the simplified diagram of FIG. 4. Consider the focused ultrasound beam 401 directed toward blood 411 moving in a blood vessel 410 that is substantially parallel to a subject's skin 405. The central ray of the beam, designated C, is substantially normal to the skin 405, so there will be no appreciable Doppler frequency shift in back-scattered energy along the path of this central ray. (For this reason, prior art Doppler techniques generally direct a beam at an angle with respect to the perpendicular to a moving material to be detected.) Next, consider the ultrasound energy at the outer extremes of the focused beam; for example, the outer rays of the focused beam designated L and R. In the example of FIG. 4, the ray L has a component in the same direction as blood flow, whereas the ray R has a component in the direction opposed to blood flow. Accordingly, the Doppler shift of ultrasound energy back-scattered toward the transducer along ray L will have a lower frequency than the originally transmitted energy (called the "carrier") whereas the Doppler shift of ultrasound energy that is back-scattered toward the transducer along ray R will have a higher frequency than the carrier.

Figure 2:
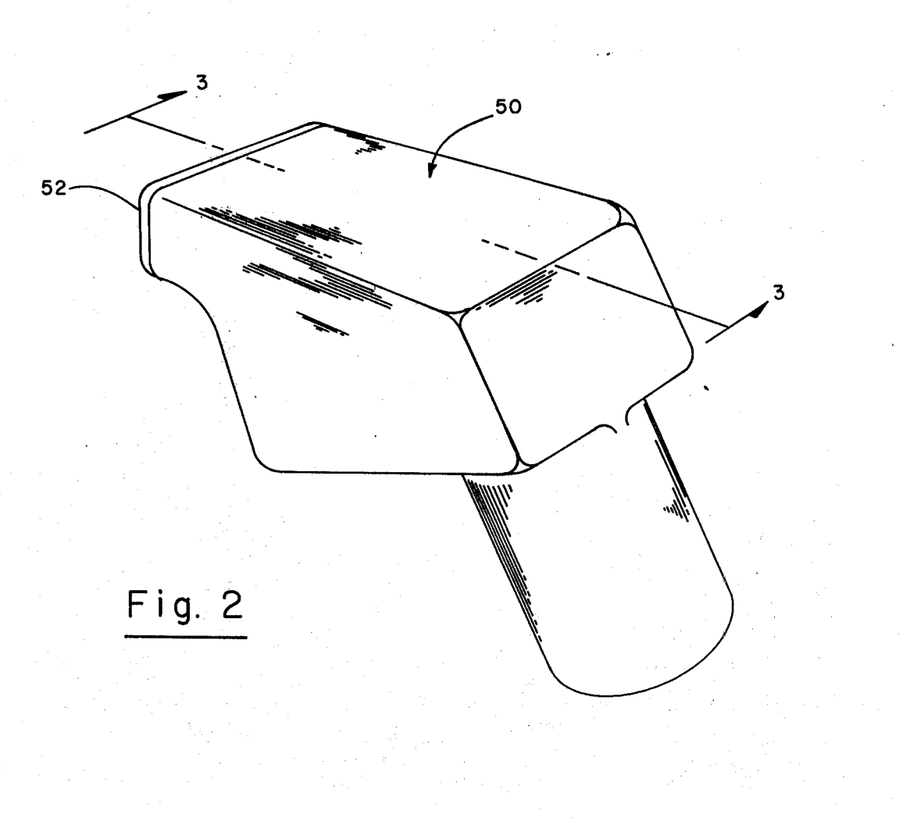
FIG. 2 is an elevational perspective view of an embodiment of the scanning module of the FIG. 1 apparatus.

These frequencies above and below the carrier frequency beat against each other, and the beats can be detected. The beat frequency is a function of the velocity of the scattering or reflecting material, and can therefore be used as a velocity indicator. For a rectangular aperture, the Doppler frequency shift, ΔF, above or below the carrier frequency can be approximated, for the simplified situation of FIG. 4, as:

$$\Delta F = (F_o V)/(2 f\# C)$$

where $F_o$ is the carrier frequency, $f\#$ is the f-number of the focused cone, C is the velocity of ultrasound in blood, and V is the blood velocity to be measured. For a round transducer, the denominator will have a factor of 2.4 rather than 2. The Doppler frequency shift is seen to be inversely proportional to the f-number of the beam cone. Therefore, for a particular focal distance, the aperture of the focused ultrasound beam will be determinative of the Doppler frequency range; the larger the aperture, the higher the frequency of operation. The transducer may have other shapes (for example, an elliptical transducer may be utilized, as set forth in my copending U.S. Application Ser. No. 890,377, assigned to the same assignee as the present application) which will modify the above Doppler frequency relationship, but the specific relationship between frequency and blood velocity can be derived empirically, even for unusual configurations. It will also be understood that while the simplified example of FIG. 4 illustrates an unreflected focused ultrasound beam, the described principles apply equally well to the embodiment of FIG. 2 wherein the beam is reflected off the reflective surface 70.

Figure 5:
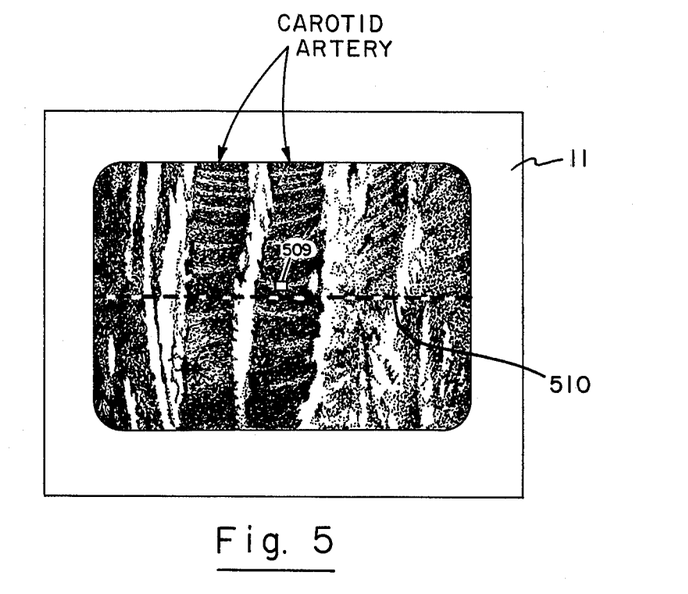
FIG. 5 illustrates a two-dimensional B-scan presentation of a cross-section through a human carotid artery.
Figure 6:
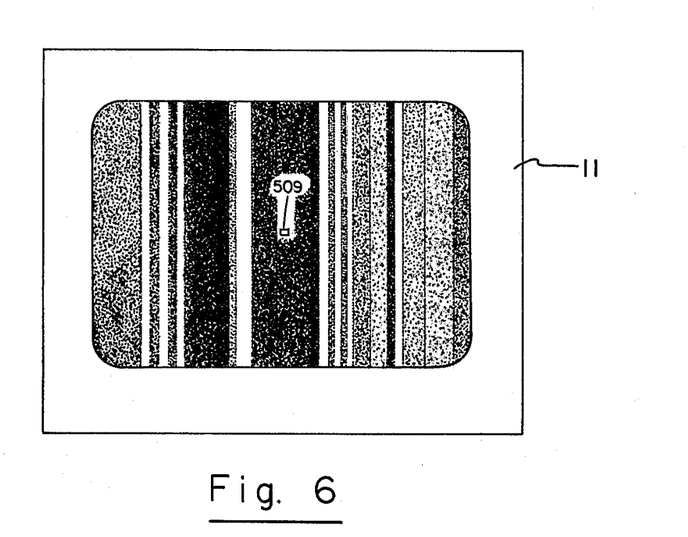
FIG. 6 illustrates a vertically spread one-dimensional B-scan presentation obtained from a single scanline of FIG. 5.

Further details of operation of the FIG. 3 system will now be described. When it is desired to obtain velocity information simultaneously with a B-scan presentation, the operator can adjust the joy stick of cursor generator 525 to position the cursor dot at an appropriate reference position in the body, as determined from the B-scan presentation. For example, in FIG. 5 a cursor dot 509 is illustrated as being positioned within the carotid artery shown in a two-dimensional B-scan cross-section taken on of a human neck. As previously explained, when blood flow velocity information is desired, the operator enables gate 545 and disables gate 540, this typically being achieved using a common switch (not shown). With reflector 70 now stopped, the B-scan presentation on display 11 becomes one-dimensional in nature; i.e., in the horizontal direction, the brightness of the display as a function of position represents the relative strength of echoes returning from successively greater depths in the body. Since the display itself continues to be two dimensional (by virtue of the display's vertical sweep), the one-dimensional brightness information will be spread out in the vertical direction, with the same information being presented on the display without regard to vertical position on the display. To illustrate, consider the approximately central vertical position on the display 11, represented by dashed line 510 in FIG. 5. This scanline of the display represents the B-scan information from the central position of the scanning mirror 70, which is also the rest position of mirror 70 when gate 540 is inactivated. After inactivation of gate 540, the resultant vertically-spread one-dimensional B-scan presentation is illustrated in FIG. 6. Thus, simply stated, FIG. 6 is a vertically spread presentation of scanline 510 of FIG. 5. As will become clear, the cursor dot, which controls the range gate for the Doppler subsystem, can be adjusted as desired at any time before and/or after inactivating gate 540.

With gate 545 having been enabled to allow Doppler subsystem detection, the bandpass filter 501 receives the broadband amplified output of pulser/receiver 130 and filters this signal to about a 1 MHz bandwidth centered at about 8 MHz, the characteristic operating frequency of transducer 80 in the present embodiment. RF detector 502 detects the envelope of the filtered signal, and range gate 503 selects an approprate time window of each echo in accordance with the cursor position selected by the operator via the joystick. The size of this time window is determined by the duration of one-shot multivibrator 530, and is typically about 1.3 microseconds (corresponding to about a 1 mm increment in the body) although it may be adjusted to correspond to any desired depth increment. The range gated output of gate 503 is coupled to audio detector 504 whose output is, in turn, coupled to audio driver 505 and speaker 506, and to frequency analyzer 507. If desired, the output of frequency analyzer 507 can be coupled to display 507 for presentation in common with the B-scan information, as represented by dashed line 507A.

The invention has been described with reference to a particular embodiment, but variations within the spirit and scope of the invention will occur to those skilled in the art. For example, while the embodiment of FIG. 3 generates a Doppler output while beam scanning has been temporarily stopped, a Doppler output could be obtained while two-dimentional B-scanning continues by employing suitable means to remove the scanning frequency. Preferably, a comb filter could be employed to filter out the scanning frequency in such case. The Doppler frequency output which would result from this system would not be the same as that from a stationary beam because of the velocity of the scanning beam itself. Comb filtering to remove the repetitive pattern can be achieved by delaying the output audio waveform by the characteristic scan time, inverting it, and adding it to the real-time signal.

I claim:

1. A method of determining the velocity of a material moving within a body, comprising the steps of:
   directing, over a given aperture, a single focused beam of ultrasound energy toward the skin of said body with the central ray of said beam oriented substantially normal to the skin;
   receiving, over the same aperture, the ultrasound beam reflected from said body;
   detecting, in the received beam, beat frequency signals resulting from the beating of Doppler effect components reflected from said moving material; and
   generating velocity-representative indications as a function of the detected beat frequency signals.

2. The method as defined in claim 1 wherein the steps of directing and receiving the ultrasound beam employ the same single transducer.

3. The method as defined by claim 2 wherein the step of detecting beat frequency signals comprises detecting beats between Doppler effected portions of the received ultrasound beam which have frequency components above and below the frequency of the originally directed ultrasound beam.

4. The method as defined by claim 3 wherein said focused beam has an f# of at least f/8.

5. The method as defined by claim 2 wherein the step of detecting beat frequency signals comprises detecting the beats between Doppler effected portions of the received ultrasound beam having components in the direction of blood flow and opposed to the direction of blood flow.

6. The method as defined by claim 2 wherein said focused beam has an f# of at least f/8.

7. The method as defined by claim 2 wherein said detecting step includes range gating.

8. The method as defined by claim 1 wherein the step of detecting beat frequency signals comprises detecting beats between Doppler effected portions of the received ultrasound beam which have frequency components above and below the frequency of the originally directed ultrasound beam.

9. The method as defined by claim 8 wherein said detecting step includes range gating.

10. The method as defined by claim 1 wherein the step of detecting beat frequency signals comprises detecting the beats between Doppler effected portions of the received ultrasound beam having components in the direction of blood flow and opposed to the direction of blood flow.

11. The method as defined by claim 1 wherein said detecting step includes range gating.

12. Apparatus for determining the velocity of blood in subcutaneous blood vessels of a body, comprising:
    an ultrasonic transducer;
    energizing/receiving means for alternately energizing the transducer and receiving energy therefrom;
    means for focusing ultrasound energy emitted by said transducer to produce a single focused beam;
    means for directing the focused ultrasound beam in a direction substantially normal to the skin of said body, and for directing ultrasound echoes back toward said transducer;
    means for detecting beat frequency signals in the output of said transducer resulting from the beating of Doppler effect components reflected from moving blood in said subcutaneous blood vessels; and
    means for generating velocity-representative indications as a function of the detected beat frequency signals.

13. Apparatus as defined by claim 12 wherein said focusing means comprises a focusing lens.

14. Apparatus as defined by claim 13 wherein said transducer, focusing means, and directing means are contained in a fluid-filled portable module.

15. Apparatus as defined by claim 14 wherein said detecting means is operative to detect beats between Doppler effected portions of the transducer output which have frequency components above and below the frequency of the ultrasound energy emitted by said transducer.

16. Apparatus as defined by claim 13 wherein said detecting means is operative to detect beats between Doppler effected portions of the transducer output which have frequency components above and below the frequency of the ultrasound energy emitted by said transducer.

17. Apparatus as defined by claim 12 wherein said transducer, focusing means, and directing means are contained in a fluid-filled portable module.

18. Apparatus as defined by claim 12 wherein said detecting means is operative to detect beats between Doppler effected portions of the transducer output which have frequency components above and below the frequency of the ultrasound energy emitted by said transducer.

19. Apparatus for imaging sections of a body by transmitting ultrasound energy into the body and determining the characteristics of ultrasound energy reflected therefrom, said apparatus having the capability of simultaneously detecting the velocity of moving material within the body, comprising:
    timing means for generating timing signals;
    energizing/receiving means alternately operative in response to said timing signals;
    a transducer coupled to said energizing/receiving means for converting energy from said energizing/receiving means into a beam of ultrasound energy and for converting reflected ultrasound energy to electrical signals;
    focusing means for focusing said beam of ultrasound energy to produce a single focused beam;

means for directing said focused ultrasound beam in a direction substantially normal to the skin of said body and for directing ultrasound echoes back toward said transducer;

first processing means responsive to the output of said energizing/receiving means for generating image-representative signals representative of the ultrasound echo characteristics of said body;

second processing means responsive to the output of said energizing/receiving means for detecting beat frequency signals resulting from the beating of Doppler effect components reflected from moving material within said body; and means for generating velocity-representative indications as a function of the detected beat frequency signals.

20. Apparatus as defined by claim 19 wherein said focusing means comprises a focusing lens.

21. Apparatus as defined by claim 20 wherein said second processing means is operative to detect beats between Doppler effected portions in the output of said energizing/receiving means which have frequency components above and below the frequency of the ultrasound energy emitted by said transducer.

22. Apparatus as defined by claim 19 wherein said transducer, focusing means, and directing means are contained in a fluid-filled portable module.

23. Apparatus as defined by claim 22 wherein said directing means comprises a scanning mirror in said fluid.

24. Apparatus as defined by claim 23 further comprising means synchronized with said timing signals for scanning said reflective scanner, and operator-controllable means for disabling said reflective scanner when said second processing means is operative.

25. Apparatus as defined by claim 27 further comprising operator-controllable cursor generating means; means synchronized with said cursor generating means for displaying an operator-selected cursor indication in conjunction with display of said image-representative signals; and means synchronized with said cursor generating means for range gating said second processing means.

26. Apparatus as defined by claim 20 wherein said transducer, focusing means, and directing means are contained in a fluid-filled portable module.

27. Apparatus as defined by claim 26 wherein said directing means comprises a scanning mirror in said fluid.

28. Apparatus as defined by claim 27 further comprising means synchronized with said timing signals for scanning said reflective scanner, and operator-controllable means for disabling said reflective scanner when said second processing means is operative.

29. Apparatus as defined by claim 28 further comprising operator-controllable cursor generating means; means synchronized with said cursor generating means for displaying an operator-selected cursor indication in conjunction with display of said image-representative signals; and means synchronized with said cursor generating means for range gating said second processing means.

30. Apparatus as defined by claim 26 wherein said second processing means is operative to detect beats between Doppler effected portions in the output of said energizing/receiving means which have frequency components above and below the frequency of the ultrasound energy emitted by said transducer.

31. Apparatus as defined by claim 19 wherein said second processing means is operative to detect beats between Doppler effected portions in the output of said energizing/receiving means which have frequency components above and below the frequency of the ultrasound energy emitted by said transducer.

* * * * *